(12) United States Patent
Fabrega et al.

(10) Patent No.: US 7,070,172 B2
(45) Date of Patent: Jul. 4, 2006

(54) METHOD AND DEVICE FOR THE EVAPORATION OF VOLATILE SUBSTANCES THROUGH A MEMBRANE

(75) Inventors: Ruben Garcia Fabrega, Barcelona (ES); Andrea Caserta, Barcelona (ES); David Moreno Perez, Barcelona (ES)

(73) Assignee: DBK España, S.A., Barcelona (ES)

( * ) Notice: Subject to any disclaimer, the term of this patent is extended or adjusted under 35 U.S.C. 154(b) by 173 days.

(21) Appl. No.: 10/809,271

(22) Filed: Mar. 25, 2004

(65) Prior Publication Data

US 2005/0127538 A1   Jun. 16, 2005

Related U.S. Application Data

(63) Continuation of application No. PCT/ES03/00628, filed on Dec. 12, 2003.

(51) Int. Cl.
*B01F 3/04* (2006.01)

(52) U.S. Cl. .................. 261/30; 261/104; 261/DIG. 88; 422/124; 239/59

(58) Field of Classification Search .................. 261/30, 261/104, DIG. 88; 422/124; 239/58, 59
See application file for complete search history.

(56) References Cited

U.S. PATENT DOCUMENTS 4,339,079 A    7/1982   Sato et al.
4,523,870 A    6/1985   Spector
5,527,493 A  * 6/1996   McElfresh et al. ........... 261/30
6,610,254 B1 * 8/2003   Furner et al. ................ 422/123

FOREIGN PATENT DOCUMENTS

EP   1319543 A1   6/2003
ES    261291 U    5/1982
ES   2020314 B3   8/1991

* cited by examiner

*Primary Examiner*—Robert A. Hopkins
(74) *Attorney, Agent, or Firm*—Michael Best & Friedrich LLP

(57) ABSTRACT

The present invention is related to devices for evaporating volatile substances in a closed environment, without the use of electric power, heating elements or absorption wicks, for the purpose of simplifying and maximally reducing the cost of the device, but at the same time maintaining its efficacy and also allowing the user to be able to adjust at will the degree of evaporation of said product. For that purpose, the evaporator device uses a vapor permeable membrane as the element responsible for causing the evaporation of the product to be evaporated. The device is especially intended to be used with the cooperation of an air current with a suitable temperature enhancing the evaporation and diffusion of the volatile substance, such as the ventilation air outlet of a vehicle, for example. The volatile substance consists in an air-freshening product, insecticide or the like. The invention is also related to a method for the evaporation of volatile substances through a membrane.

25 Claims, 9 Drawing Sheets

METHOD AND DEVICE FOR THE EVAPORATION OF VOLATILE SUBSTANCES THROUGH A MEMBRANE

This application is a continuation of International Patent Application No. PCT/ES03/00628 filed Dec. 12, 2003.

OBJECT OF THE INVENTION

The present invention is related to devices for the evaporation of volatile substances in a closed environment, without using electric power, heating elements or absorption wicks, for the purpose of simplifying and accordingly maximally lowering the cost of the device, but at the same time maintaining its efficacy and also allowing the user to be able to adjust at will the degree of evaporation of said product.

Therefore, the evaporator device uses a vapor permeable membrane as the element responsible for causing the evaporation of the product to be evaporated.

The device is especially intended for being used with the cooperation of an air current with a temperature suitable for enhancing the evaporation and diffusion of the volatile substance, such as the ventilation air outlet in a vehicle.

The volatile substance, preferably in a liquid state, consists in an air-freshening product, insecticide or the like.

The invention is also related to a method for the evaporation of volatile substances through a membrane.

BACKGROUND OF THE INVENTION

Perfuming and/or insecticide substance evaporator devices are known which, for said purpose, are provided with electric heating means, such as PTC resistances, radiating heat energy for the purpose of enhancing or forcing the evaporation of a volatile substance, which can be found, for example, in a liquid state, or impregnated in a porous material wafer.

The use of porous material or absorbent wicks is also known, which are inserted in a recipient containing the substance in liquid state to be evaporated, which impregnates and moves upwards due to capillarity through said wick to be led to one end of the wick, where evaporation of the substance occurs. The evaporation in said region can occur naturally, i.e. not forced, or with the cooperation of the aforementioned heating means or by means of a forced air current.

The design and manufacture of this type of devices is basically conditioned by achieving a low-cost, easy to manufacture simple product which, at the same time, provides the user with maximum use efficacy and comfort.

DESCRIPTION OF THE INVENTION

One of the aspects of the invention refers to an air-freshening device through a membrane with an adjustable degree of evaporation, in which an air flow with a suitable temperature cooperates in the evaporation of a volatile substance, which comprises a container for at least one type of volatile substance, a strip of vapor permeable material in contact with said volatile substance, which is exposed to said air flow. The device also comprises a casing supporting said container and said vapor permeable strip, and keeps them under the influence of said air flow, as well as means for adjusting the degree of evaporation of said substance by means of controlling the air flow acting on said strip.

Said air flow is preferably at a temperature suitable for enhancing the evaporation of said substance. Suitable temperature must be understood as any temperature having the effect of speeding up the degree of evaporation of the substance.

The vapor permeable strip is a liquid impermeable evaporation membrane adhered to said container for the volatile substance forming an air-freshening unit, such that one of the faces of the strip is partially in direct contact with the volatile substance, and the other face is partially in direct contact with the environment. The volatile substance is preferably an aromatic substance, although substances with another type of properties, such as insecticide substances for example, can also be used.

The device adjustment means are placed between the air flow and the external face of the permeable strip, and are provided with at least one window of a variable area for controlling the amount of air passing through the device and acting on the membrane and, as a result, the amount of air-freshening product supplied to the environment per unit of time.

The device is optionally provided with side windows, the area of which can also be adjusted, preferably simultaneously to the aforementioned windows of a variable area.

The device is complemented with means for fixing to a fixed structure, such as the grating of a ventilation air equipment outlet, for example, such as the ventilation air outlet of a motorized vehicle, or an air-conditioning equipment. In such case, the aforementioned air flow comes from the ventilation air outlet of a vehicle, or of an air-conditioning equipment.

An evaporator device of great simplicity, and therefore of a very reduced cost, is thus obtained, such that it can be used and disposed of, i.e. single use. Alternatively, the parts forming said casing can be removable for the purpose of replacing the air-freshening unit when the volatile substance has depleted.

Another aspect of the invention refers to a method for adjustably evaporating a volatile substance, which comprises putting said volatile substance into contact with a strip of vapor permeable material, and projecting an air follow on said strip, controlling the air flow acting on said strip and, as a result, the amount of evaporated substance projected into the environment.

Control of said air flow acting on said strip is carried out by modifying the area which the air flow must pass through before acting on said strip.

Modification of the area for the passage of the air flow can be carried out by moving two parts, relatively to one another, each one of which is provided with at least one window, and making said windows overlap to a greater or lesser extent.

The degree of evaporation of the substance is also adjusted by means controlling, either in a natural or forced manner, the temperature of the air flow.

DESCRIPTION OF THE DRAWINGS

To complement the description being made and for the purpose of helping to better understand the features of the invention, according to a preferred practical embodiment thereof, a set of drawings is attached as an integral part of said description which, with an illustrative and non-limiting character, show the following:

FIG. 9 shows an upper plan view of the device without the front casing in FIG. (9a), and a lower plan view in FIG. (9b).

FIG. 12 shows respective elevational views in figures (a) and (b) of the device in different positions. Figure (c) shows an upper plan view, and figure (d) shows a perspective view of the device. All the views show the product without being activated, i.e. without removing the protective strip of the membrane.

FIG. 13(a) shows a similar representation of FIG. 10, and FIG. (13b) shows a similar representation of FIG. 11, wherein it is represented a further embodiment of the invention in which the resilient taps are not an integral part of the device.

PREFERRED EMBODIMENT OF THE INVENTION

Figures 1, 2:
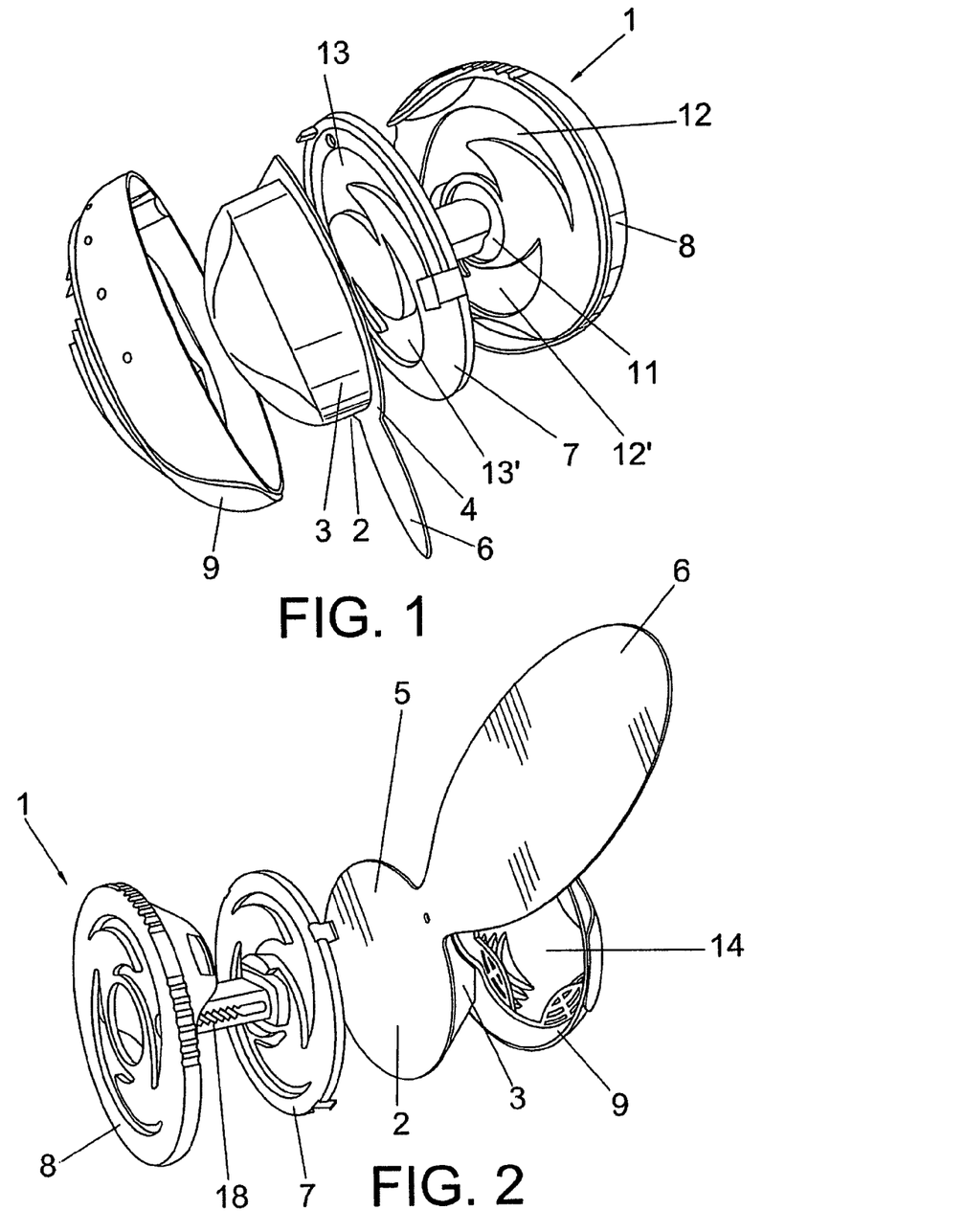
FIG. 1 shows a front and side exploded perspective view of the parts making up the device object of the invention.
FIG. 2 shows a rear and side exploded perspective view of the parts making up the device object of the invention.

In view of the figures indicated, it can be seen how in one preferred embodiment of the invention, the evaporator device (1) comprises an air-freshening unit (2) formed by a container (3) housing the volatile substance to be evaporated, which is preferably in a liquid state. The container (3), having a float cup shape as can be seen in FIG. 1, for example, is hermetically sealed by an evaporation membrane (4) such that the volatile substance is in direct contact with one majority part of the internal face of the membrane (4), which is liquid impermeable such that it prevents any spillage, but is vapor permeable, therefore allowing the evaporation of the liquid it retains. The container (3) is manufactured from a heat-formed plastic material.

A protective strip (5) is arranged on the outer face of the membrane (4), preventing the evaporation of the substance prior to using the device, for which purpose said strip is easily removable and partially extends outside of the device (1), forming a tab (6) facilitating its removal after removing the front part (9) for being able to access it. This protective strip (5) must be partially folded over itself and project on one side, such that the protective strip (5) can be easily removed from that side from the exterior of the product without needing to remove the front part (9).

This preferred embodiment of the device (1) comprises an intermediate part (7), a rear part (8) and a front part (9), all of them having a circular configuration. Parts (7) and (8) are overlapped, coupled to one another by clipping and with a relative rotational capability between them, for which purpose the part (7) is provided with several flaps (10) which are inserted, by resilient coupling, in a central hole (11) existing on the rear part (8), as can especially be seen in FIG. 3.

The intermediate part (7) and the rear part (8), having a disc-shaped configuration, constitute the degree of evaporation adjustment means, therefore said parts are placed between the air flow and the outer face of the permeable strip, and are provided with windows for the passage of the air flow. Specifically, part (8) is provided with windows (12), (12'), and part (7) is provided with windows (13), (13'), all the windows preferably having the same shape.

In this embodiment, the windows have a semi-circular tendency.

Figure 3:
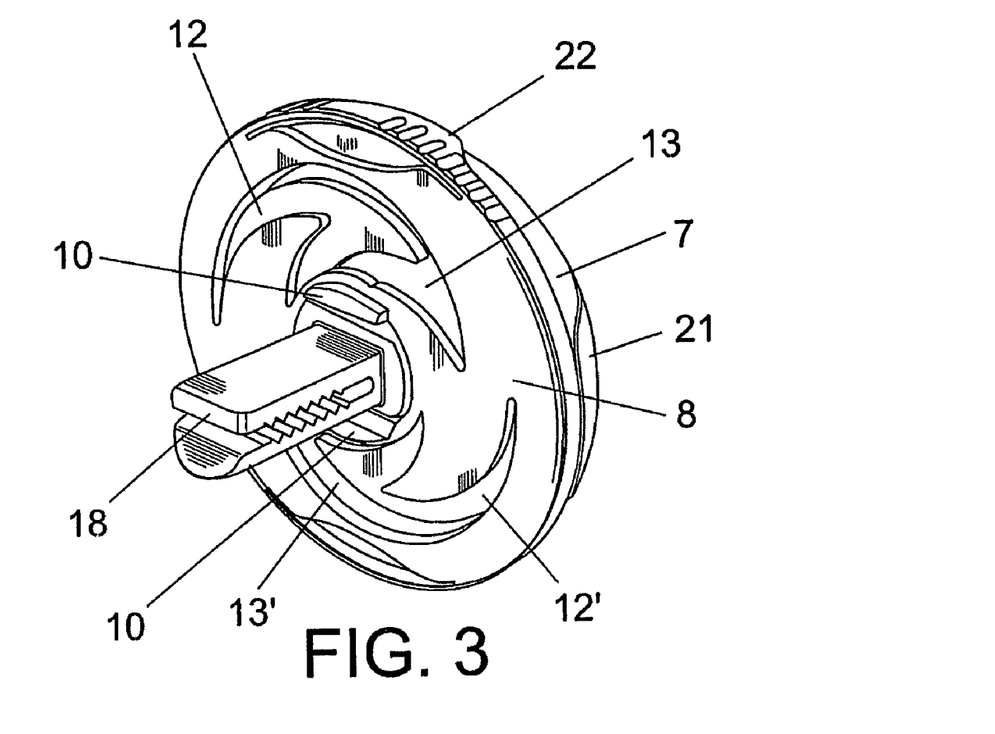
FIG. 3 shows a rear and side perspective view of the adjustment means of the device forming part of the casing thereof.
Figure 4:
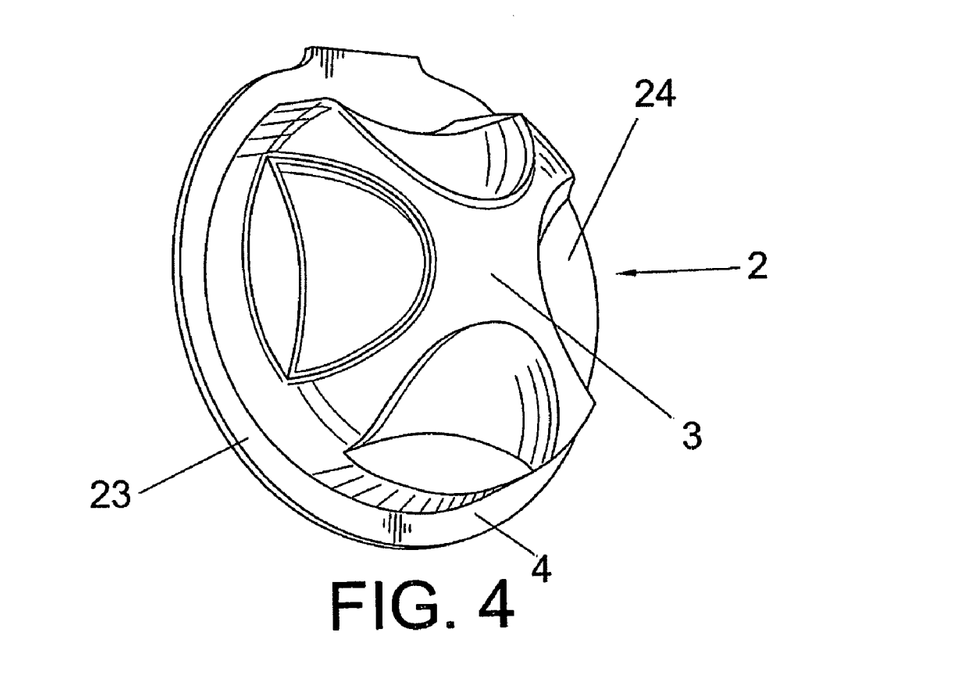
FIG. 4 shows a rear and side perspective view of the air-freshening unit when it forms a single container.

As can be seen in FIG. 3, the relative rotation between parts (7) and (8) has the effect that the windows (12,12') and (13,13') are overlapped to a greater or lesser extent, and accordingly, the passage area for the air flow the device receives by the outer face of part (8) opens or closes.

The front part (9) is assembled on the assembly formed by parts (7) and (8) by conventional means, and the air-freshening unit is enclosed inside the assembly, as seen in the figures. Said connection between the part (9) and parts (7) and (8) can be stable, in which case the device will be a single-use device, i.e. to use and dispose of. Optionally, these parts can be removable so as to allow replacing the air-freshening unit with a spare part when the air-freshening liquid has been depleted. The front part (9) is provided with a large central hole (14) through which the container (3) of the air-freshener unit (2) is visible.

To enhance the appearance of the device (1), the container (3) can be transparent and the volatile substance housed therein can be colored, for example with a color associated to the aroma said substance releases. In addition to this effect, the container (3) projects outside of the front part (9) and forms a series of recesses (24) for the purpose of also facilitating its handling by the user, and providing it with greater rigidity against frontal pressure.

Since the device is especially indicated for use thereof under the influence of a hot air current, the materials with which it is manufactured, and particularly the materials of the container (3), have been carefully selected to withstand temperatures comprised between 75 and 80° C.

Figure 5:
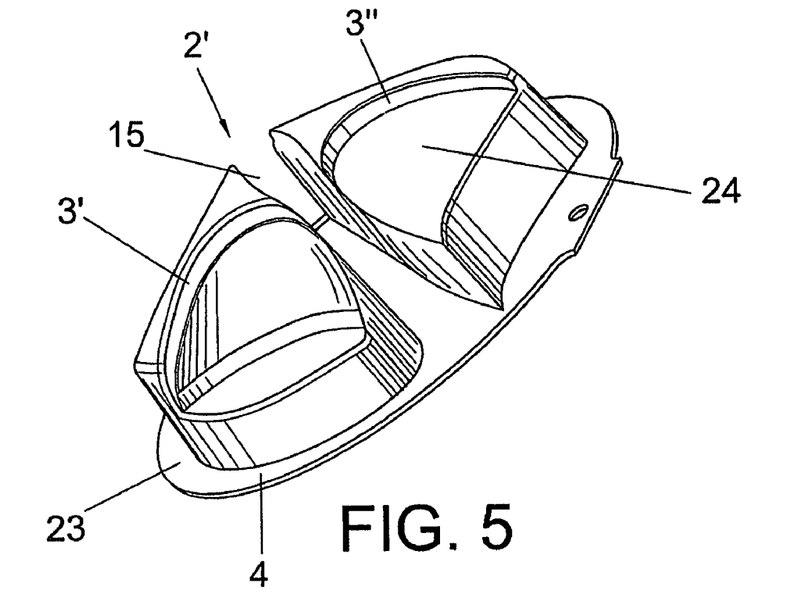
FIG. 5 shows a side perspective view of the air-freshening unit when it forms two independent containers.
Figure 6:
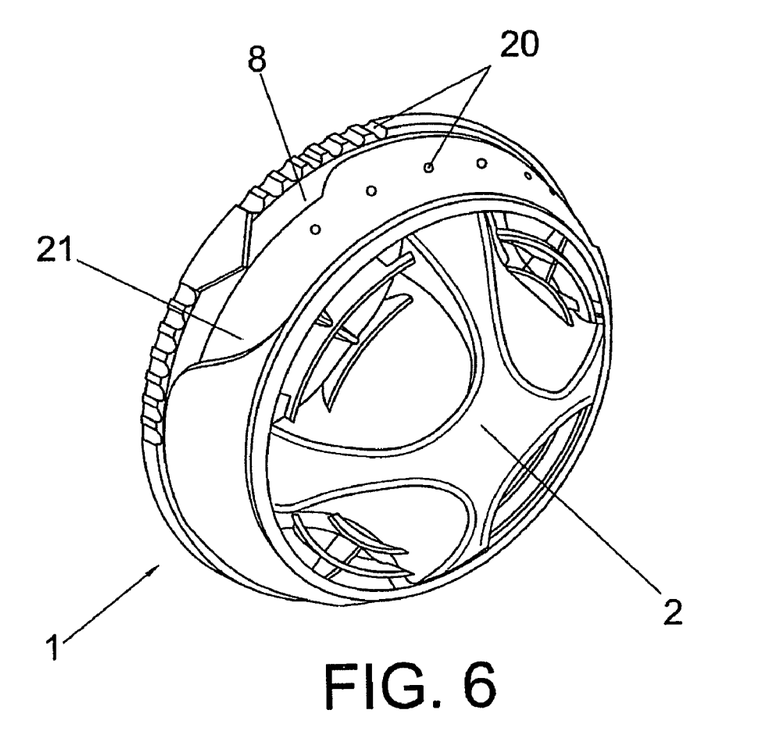
FIG. 6 shows a perspective view of the evaporation device with all its components coupled together when the air-freshening unit forms a single container.
Figure 7:
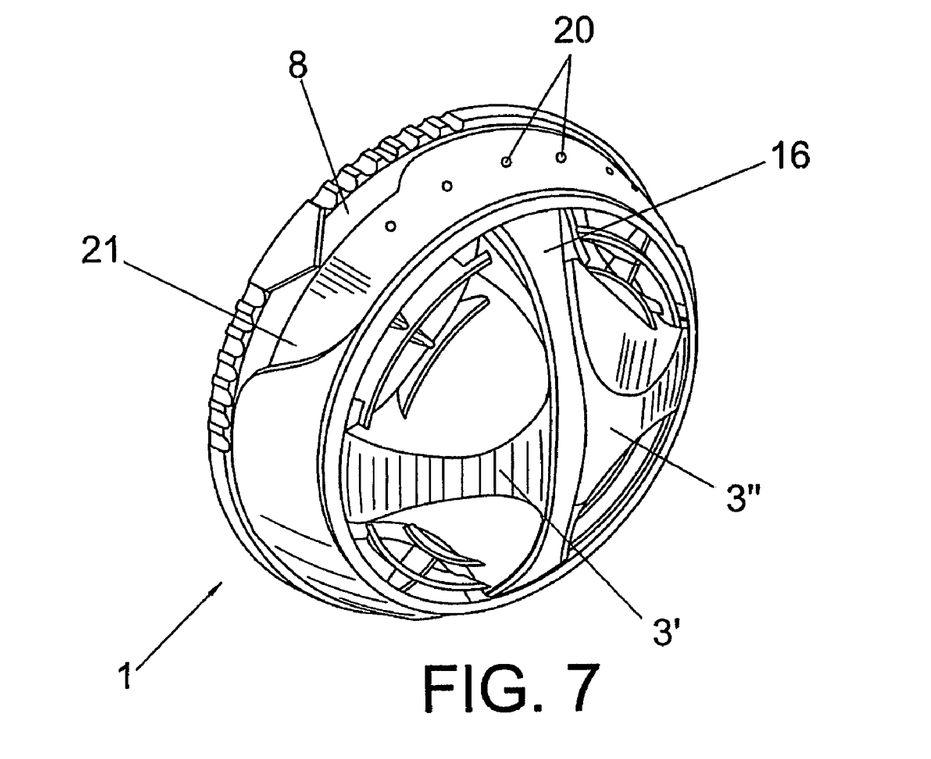
FIG. 7 shows a perspective view of the evaporation device with all its components coupled together when the air-freshening unit forms two containers.
Figure 8:
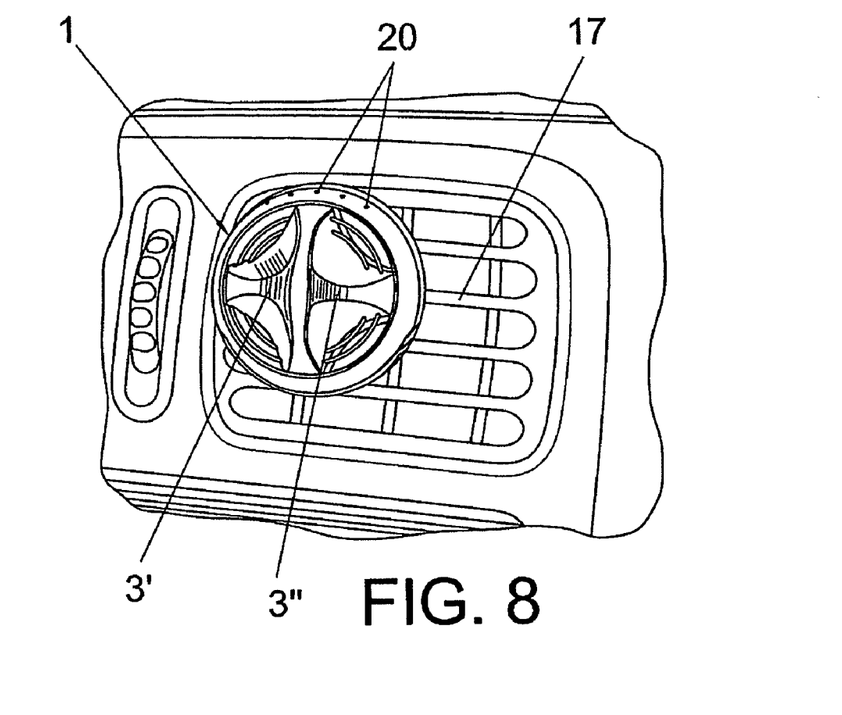
FIG. 8 shows a perspective view of the evaporation device when in use coupled to a ventilation grating of a vehicle when the air-freshener forms two containers.
Figure 9:
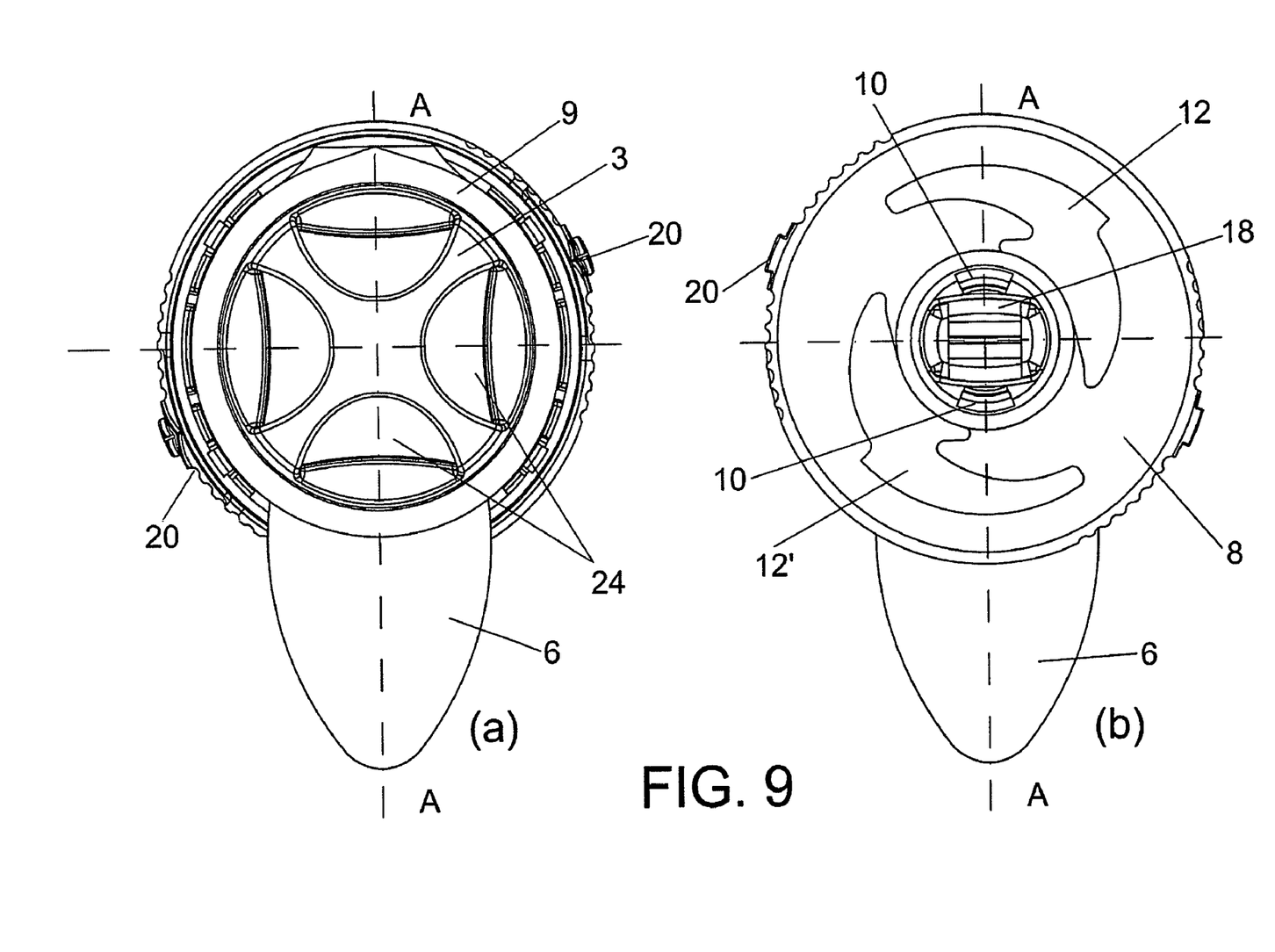
Figure 10:
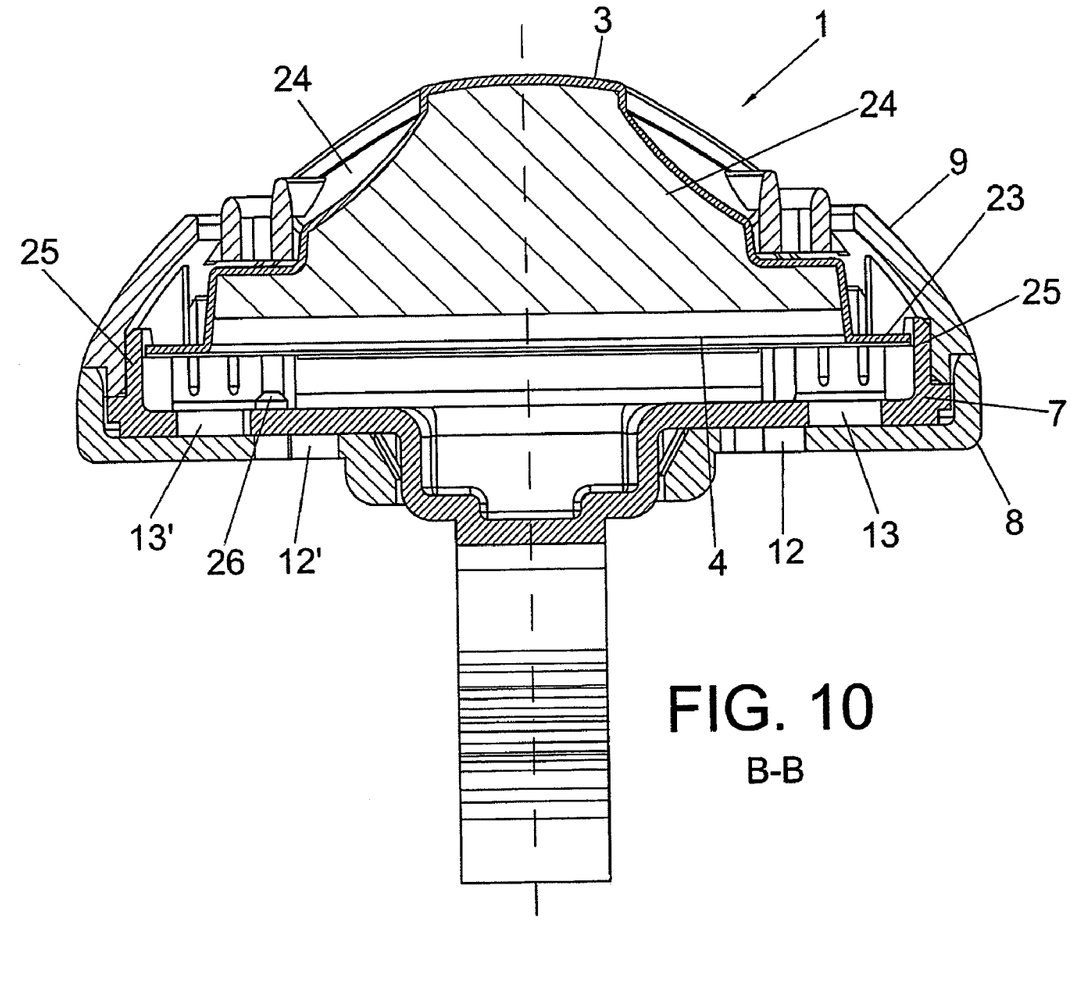
FIG. 10 shows an elevational view of the device according to a section taken along the B—B line of FIG. (12c).

In one embodiment shown in FIGS. 5, 7 and 8, the container (3) can be split into two independent compartments (3') and (3"), and the substance housed in each compartment can be of a different nature than that of the other compartment, either in reference to its color, aroma or even to an active ingredient in its composition. Thus, two substances having a different aroma can be provided, providing the user with the option of using different aromas in a single evaporator device. In said case, the membrane (4) and the protective strip (5) are split in two to permit the independent activation of each one of the aromatic substances. To obtain the simultaneous evaporation of the two types of substances, the membrane (4) is common to both compartments, and the aroma generated will be the mixture of both substances.

The two compartments (3), (3') define a groove (15) between them, and the front part (9) is provided in such case with a rib (16) housed in said groove, as shown in FIG. 7.

The device (1) comprises fixing means for fixing it to a fixed structure, such as the grating (17) of the air outlet of a ventilation unit of a vehicle, as shown in FIG. 8, such that the device (1) is emerged in the air current generated, part of which passes through the device. In a similar manner, the device could be applied on an air-conditioning equipment.

The device is complemented with fixing means for fixing it on said grating (17), consisting in flexible tabs (18) which, acting like a gripping device, can be stably coupled to said grating (17). In one embodiment the resilient tabs (18) are integral to the intermediate part (7) and pass through the rear part (8) through the hole (11), such that this intermediate part (7) remains fixed during the adjustment and the rear part (8) is the part which rotates to cause the adjustment.

Figure 13:
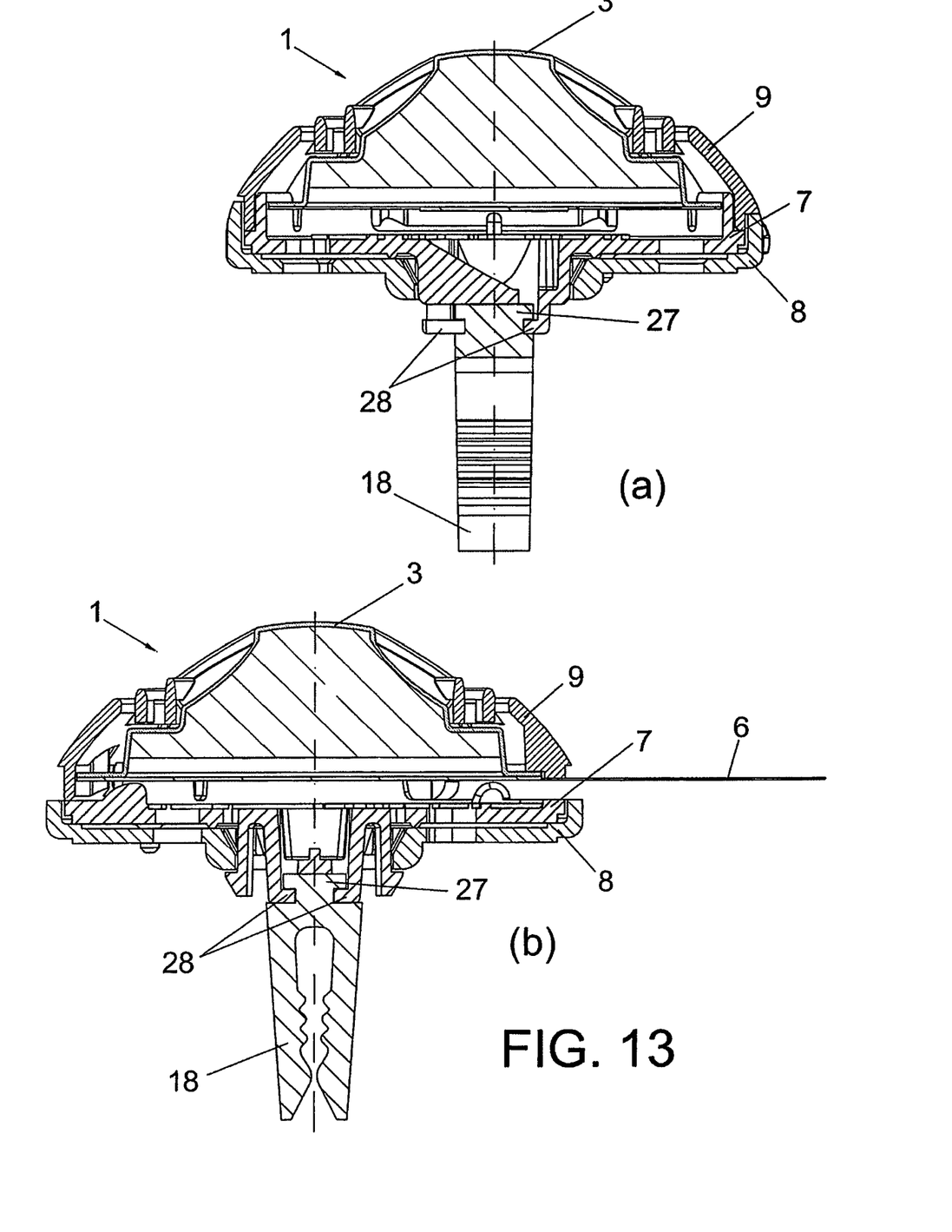

In a further embodiment of the invention represented in FIG. 13, the resilient taps (18) are not an integral part of the device, instead they consist of an independent piece which can be easily coupled to the device be means of a projection (27) meant to be anchored into fingers (28). In this embodiment the device can be more efficiently stored and transported, because the resilient taps (18) are not coupled to the device until it is used for the first time, for that the device presents a reduced volume.

Figure 11:
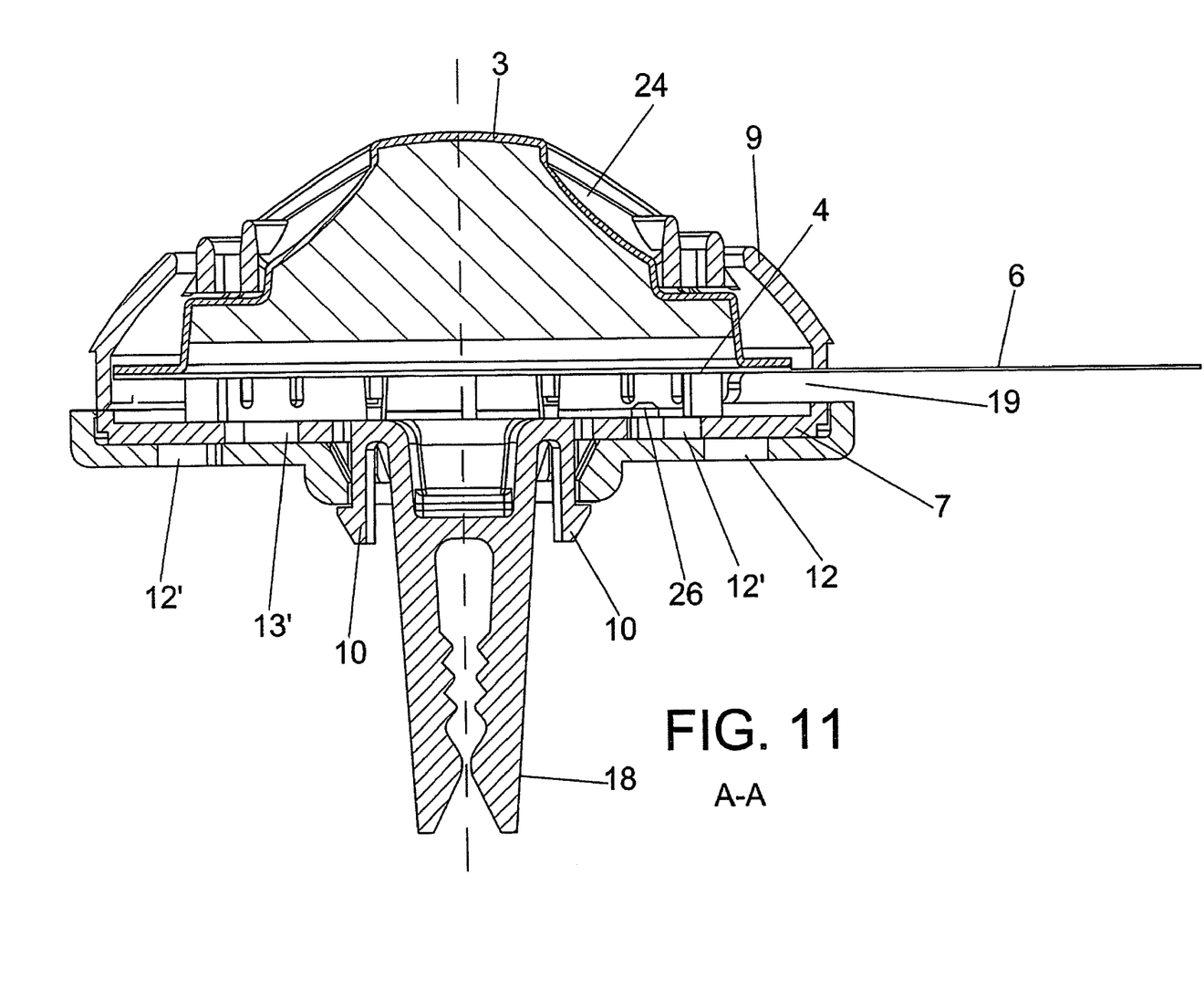
FIG. 11 shows an elevational view of the device according to a section taken along the A—A line of FIG. (9b).
Figure 12:
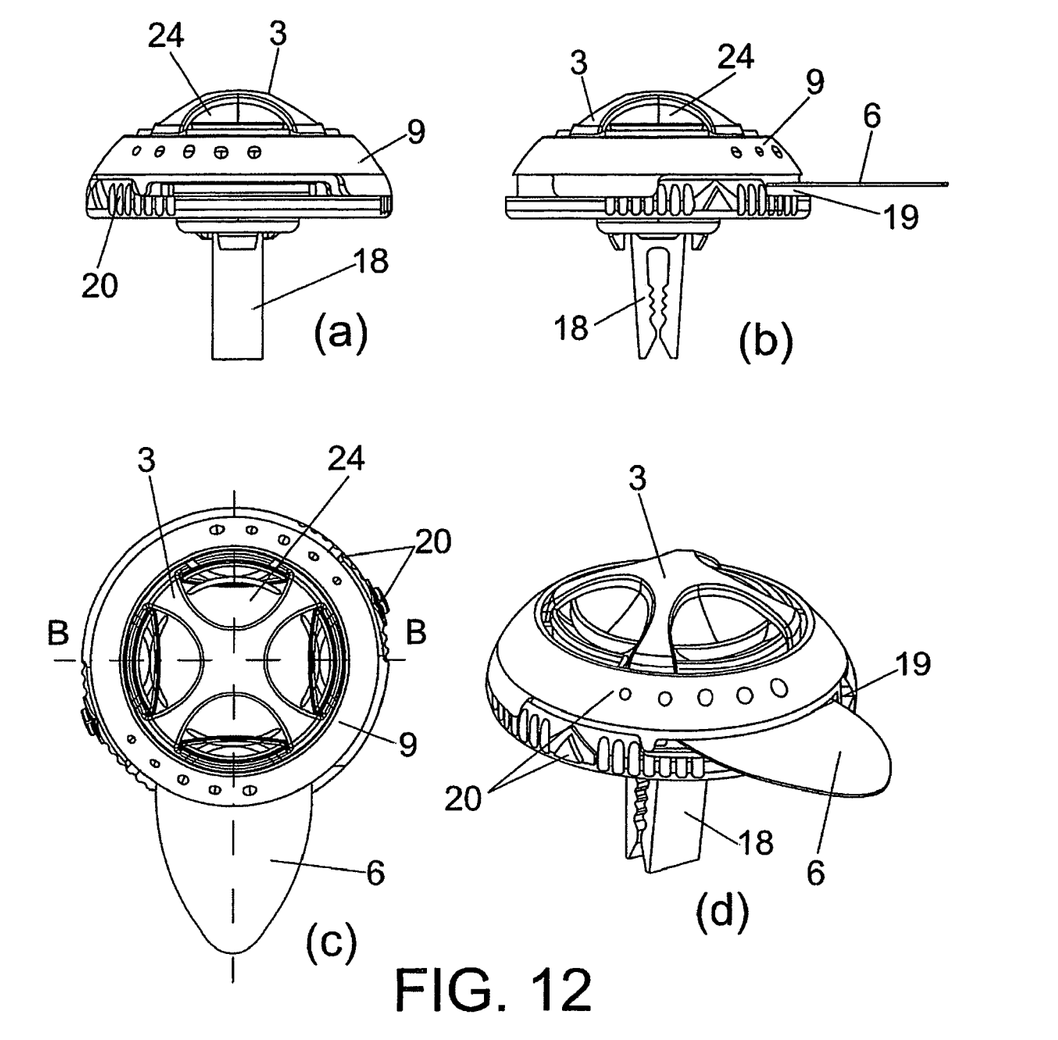

The evaporated product is diffused towards the sides of the device in 360°, for which purpose it has at least one side window (19) carried out by means of the corresponding opening on the front part (9), as seen in FIG. 11. The intermediate part (7) forms a perimetral wall (25) also having openings, such that when the openings coincide with the side window (19), the outlet of the evaporated product is allowed through the side. Thus, at the same time that the rear windows (12) and (13) open, the side windows (19) open, thus allowing the air current to enter or circulate between the rear windows (12), (13) and the side windows (19), impelling the evaporated product.

A graduated scale (20) allows the user to identify the degree of opening of the windows and therefore the degree of evaporation selected between a maximum and minimum. The rotation allowed between parts (7) and (8) in this preferred embodiment is 90°. The end run stop for graduating the evaporation consists in several stops (21) on which several projections (22) act and two internal stops (26) acting on a corner of the rear windows (12), (13).

The device (1) has a circular configuration, therefore it can be placed in any angular position. It can also be placed on a horizontal as well as vertical grating, without this affecting its operation.

In this preferred embodiment, it is seen how in the device (1), the membrane adopts a transverse arrangement with regard to the feed direction of the air flow. However, in other possible embodiments, said arrangement of the membrane could have a certain tilt with regard to the air flow.

In view of this description and set of figures, a person skilled in the art could understand that the embodiments of the invention which have been described can be combined in multiple manners within the object of the invention. The invention has been described according to several preferred embodiments thereof, but for the person skilled in the art it will be evident that variations can be introduced in said preferred embodiments without exceeding the object of the claimed invention.

The invention claimed is:

1. A device for air freshening through a membrane with an adjustable degree of evaporation, wherein an air flow cooperates in the evaporation of a volatile substance, comprising:
    a container of at least one type of volatile substance;
    a strip of vapor permeable material in contact with said volatile substance, said strip being exposed to said air flow;
    a casing supporting said container and said strip of vapor permeable material to keep them under the influence of said air flow; and
    adjustment means for adjusting the degree of evaporation of said substance by means of a control of the air flow acting on said strip; wherein the adjustment means comprises an intermediate part and a rear part overlapped and with relative rotational capability between one another, said intermediate part and said rear part each comprising at least one window, such that with the relative rotation between both parts, the windows partially overlap to a greater or lesser extent, thus varying the area through which said air flow circulates.

2. A device according to claim 1, wherein the vapor permeable strip comprises a liquid impermeable evaporation strip adhered to said container of the volatile substance forming an air-freshening unit, such that one of the faces of the strip is at least partially in direct contact with the volatile substance, and the other face is at least partially in direct contact with the environment.

3. A device according to claim 1, wherein the adjustment means are between the air flow and the outer face of the permeable strip, said adjustment means being provided with at least one window of variable area for the passage of the air flow.

4. A device according to claim 1, wherein the windows of the intermediate and rear parts have the same shape.

5. A device according to claim 1, wherein said casing comprises a front part overlapping said intermediate part, and in that the air-freshening unit is enclosed between said front and intermediate part.

6. A device according to claim 5, wherein the front part and intermediate part are connected in a removable manner, allowing the replacement of the air-freshening unit.

7. A device according to claim 5, wherein the casing, the container, and the vapor permeable strip comprises a circular configuration.

8. A device according to claim 5, wherein the front part comprises a central opening through which the container of the air-freshening unit is visible.

9. A device according to claim 5, wherein the container is transparent and the volatile substance housed therein is colored.

10. A device according to claim 9, comprising fixing means provided for fixing the container to a fixed structure.

11. A device according to claim 10, wherein grating of the ventilation equipment air outlet comprises the structure.

12. A device according to claim 11, wherein the ventilation air outlet of a motorized vehicle comprises the grating.

13. A device according to claim 10, wherein the fixing means consist in resilient tabs capable of being stably coupled to said grating.

14. A device according to claim 5, wherein the fixing means are integral to the intermediate part and pass through the rear part, such that this intermediate part remains fixed during the adjustment and the rear part is rotational.

15. A device according to claim 10, wherein the fixing means comprise an independent component of the device.

16. A device according to claim 5, wherein the container comprises two independent compartments and in that each compartment houses a volatile substance having a different nature than the one in the other compartment.

17. A device according to claim 16, wherein the substances have a different color.

18. A device according to claim 16, wherein the substances produce a different aroma.

19. A device according to claim 16, wherein the two compartments define a groove between one another, and in that the front part is provided with a rib housed in said groove.

20. A device according to claim 1, wherein the casing comprises side windows facilitating the air outlet, and in that the adjustment of the area of these windows is simultaneous to that of the windows of the intermediate and rear parts.

21. A device according to claim 16, wherein the permeable strip comprises a protective strip adhered to its outer face intended for preventing the evaporation of the volatile substance prior to using the evaporator device.

22. A device according to claim 21, wherein the protective strip partially extends outside the device, forming a tab facilitating its removal.

23. A device according to claim 16, wherein the air flow comes from the ventilation air outlet of a vehicle.

24. A device according to claim 16, wherein the air flow comes from an air-conditioning equipment.

25. A device according to claim 16, wherein the air comprises a suitable temperature for enhancing the evaporation of the volatile substance.

* * * * *